United States Patent
Sun et al.

(10) Patent No.: US 6,225,633 B1
(45) Date of Patent: May 1, 2001

(54) PHOTO-IONIZATION DETECTOR FOR VOLATILE GAS MEASUREMENT AND A METHOD FOR SELF-CLEANING THE SAME

(75) Inventors: Hong T. Sun, Sunnyvale; Peter C. Hsi, Fremont, both of CA (US)

(73) Assignee: RAE Systems, Inc., Sunnyvale, CA (US)

(*) Notice: Subject to any disclaimer, the term of this patent is extended or adjusted under 35 U.S.C. 154(b) by 0 days.

(21) Appl. No.: 09/177,669

(22) Filed: Oct. 22, 1998

(51) Int. Cl.[7] ........................................... G01N 27/64
(52) U.S. Cl. ........................ 250/389; 250/374; 250/281
(58) Field of Search ........................... 250/389, 374, 250/281, 288

(56) References Cited

U.S. PATENT DOCUMENTS

| | | |
|---|---|---|
| 4,013,913 | 3/1977 | Driscoll et al. . |
| 4,376,893 * | 3/1983 | Whetten ............................ 250/374 |
| 4,398,152 | 8/1983 | Leveson . |
| 4,429,228 * | 1/1984 | Anderson .......................... 250/374 |
| 4,704,536 | 11/1987 | Sugiyama et al. . |
| 4,778,998 | 10/1988 | Carnahan . |
| 4,804,846 | 2/1989 | Hall . |
| 5,028,544 * | 7/1991 | Rasulev et al. ................... 250/389 |
| 5,393,979 | 2/1995 | Hsi . |
| 5,431,714 | 7/1995 | Burtscher et al. . |
| 5,504,328 * | 4/1996 | Bonser .............................. 250/288 |
| 5,520,060 * | 5/1996 | Gysi et al. ......................... 73/865.8 |
| 5,540,898 * | 7/1996 | Davidson ........................ 422/186.15 |
| 5,572,137 | 11/1996 | Jones . |
| 5,604,059 * | 2/1997 | Imura et al. ........................... 430/5 |
| 5,728,586 | 3/1998 | Platzer . |
| 5,733,833 | 3/1998 | Abe et al. . |
| 5,773,833 | 6/1998 | Hsi . |
| 5,855,850 | 1/1999 | Sittler . |
| 5,968,837 * | 10/1999 | Doring et al. ...................... 250/281 |

FOREIGN PATENT DOCUMENTS

| | | | |
|---|---|---|---|
| 4320607 | 12/1994 | (DE) | G01N/27/64 |
| 19750788 | 6/1999 | (DE) | H01J/47/02 |
| 0524022 | 1/1993 | (EP) | G01N/27/66 |
| 0694783 | 1/1996 | (EP) | G01N/27/66 |
| 1042359 | 9/1966 | (GB) | H01J/37/32 |

OTHER PUBLICATIONS

Patent Abstract of Japan Publication No. 60066155 (Shimazu Seisakusho KK), Apr. 16, 1985.

* cited by examiner

Primary Examiner—Constantine Hannaher
Assistant Examiner—Otilia Gabor
(74) Attorney, Agent, or Firm—Skjerven Morrill MacPherson LLP; David Millers

(57) ABSTRACT

A photo-ionization detector (PID) includes an ultraviolet (UV) lamp that transmits UV light into an ionization chamber to ionize volatile gases. An ion detector in the ionization chamber includes interdigital electrodes that collect resulting ions using an electrical field perpendicular to the UV light propagation. A pump in the PID circulates gases through the ionization chamber in a direction perpendicular to the electrical field and to the UV light propagation. The PID additionally provides a UV monitor having interdigital electrodes that release electrons when struck by the UV light. The size of a monitor current in the UV monitor indicates the intensity of the UV light. The UV monitor is in a UV monitor chamber that protects the UV monitor from exposure to the ionized gases and improves the accuracy of UV intensity measurements. The interdigital electrodes of the ion detector and the UV monitor can be manufactured by forming an electrode layer on a substrate and selectively patterning the electrode layer to produce interdigital electrodes. If the substrate is not transparent to UV light, the substrate can be removed or patterned to match the interdigital electrodes. To remove contamination in the PID, the pump is turned off while operation of the UV lamp continues. The UV light creates ozone that accumulates in the ionization chamber and removes contamination from the ionization chamber.

39 Claims, 5 Drawing Sheets

PHOTO-IONIZATION DETECTOR FOR VOLATILE GAS MEASUREMENT AND A METHOD FOR SELF-CLEANING THE SAME

BACKGROUND OF THE INVENTION

1. Field of the Invention

This invention relates to volatile gas detectors and particularly to a portable photoionization detector (PID).

2. Description of the Related Art

Photo-ionization detectors (PID) can detect volatile organic gases or compounds. A conventional portable PID 10 is illustrated in FIG. 1. PID 10 includes an ultraviolet (UV) lamp 12, which produces high energy photons having an energy above 9.2 electron volts (eV). The high energy photons from UV lamp 12 are directed into an ionization chamber 14 through an optical window 16. The some of the photons collide with molecules of volatile gases having ionization potentials below the energy of the photons. Such collision ionizes the molecules, creating detectable ions and electrons.

PID 10 additionally includes an ion detector 18 having a pair of electrodes 20 and 22. Ion detector 18, typically made of a metal, has a high voltage (e.g., greater than 150 V) applied across electrodes 20 and 22 to generate an electrical field. Accordingly, first electrode 20 is electrically biased to attract positively charged particles and second electrode 22 is biased to attract negatively charged particles. Second electrode 22 repels the ions towards first electrode 20 which is simultaneously collecting the volatile gas ions. As a result, a current is produced with which the concentration of the volatile gas can be measured. The magnitude of this measurement current depends on the number of ions produced and therefore on the concentration of ionizable molecules and the intensity of the UV light in ionization chamber 14. If the UV light intensity is constant, the measurement current can be converted to the concentration, in part per million (ppm), of the volatile organic compounds.

In PID 10, there is a space 24 between optical window 16 and second electrode 22. Space 24 is a "dead zone," in which positive ions are trapped. The positive polarity of second electrode 22 prevents positive ions in space 24 from reaching first electrode 20. Accordingly, the configuration of electrodes 20 and 22 with dead space 24 inhibits the production and collection of ions and can reduce the sensitivity or accuracy of PID 10. For example, current PID devices typically can measure concentrations up to about 2,000 parts per million (ppm) of ionizable gases.

As mentioned above, the measurement current can be converted to yield the concentration of the volatile gases if the UV intensity from lamp 12 remains constant. However, UV intensity typically diminishes during the normal operation of PID 10 due to a variety of factors, including degradation of lamp 12, contamination of optical window 16, and introduction of interfering substances such as methane, carbon monoxide, or water which block or absorb UV photons in ionization chamber 14. A UV monitor 26, which is a biased electrode, is disposed in ionization chamber 14 to measure the intensity of the UV light. The UV light by striking UV monitor 26 releases electrons to produce a monitor current indicative of the intensity of the UV light. The monitor current can be used to correct for UV intensity variations when calculating the volatile gas concentration from the measurement current. The monitor current can also be used to adjust the intensity of UV lamp 12, for example, by increasing the supply voltage to lamp 12 when the monitor current indicates a low UV intensity. The monitor current, however, inaccurately measures the intensity of UV lamp 12 in the presence of ionized volatile gases. Biased monitor electrode 26 collects positive ions. As a result, the monitor current increases in the presence of ionizable gases, resulting in a less than accurate measurement of the UV intensity. Accordingly, a more accurate UV monitor is needed.

As discussed-above, contamination of PID 10, including optical window 16, reduces the UV intensity. The contamination is often a polymer-like coating caused by the deposition of metal atoms, oil film, or dust particles, during the normal use of PID 10. A user must often disassemble PID 10 to clean optical window 16. This cleaning is time consuming and burdensome. Accordingly, it is advantageous to provide a self-cleaning PID system.

SUMMARY OF THE INVENTION

The present invention provides a photo-ionization detector (PID) comprising a detector housing having an ionization chamber configured to receive volatile gases. An ultraviolet (UV) lamp transmits UV light through an optical window to ionize the volatile gases in the ionization chamber. An ion detector is disposed in the ionization chamber. The ion detector comprises a pair of differentially biased electrode structures which produce an electrical field that is perpendicular to the direction of the UV light propagation. The ion detector captures ions produced by the ionization of the volatile gases and produces a current which is used to measure the concentration of the volatile gases. A pump is also incorporated into the detector housing to circulate the gases into and out of the ionization chamber. The direction of the flow of gases is perpendicular to the direction of the electrical field and the direction of the UV light propagation. Because the aforementioned directions are perpendicular to each other, formation and collection of ions are more efficient, and the ion detector of the present invention can accurately measure concentrations up to about 10,000 ppm of ionizable gases.

In accordance with another aspect of the invention, a UV monitor, that measures the intensity of the UV light, includes a pair of monitor electrodes which release electrons when struck by the UV light. As a result, a current is induced by which the intensity of the UV light can be measured. Since capture of volatile gas ions by the monitor electrodes would interfere with measurement of the UV intensity, the UV monitor is disposed in a UV monitor chamber that prevents the monitor electrodes from being significantly exposed to the ionized gases. The UV monitor chamber has an optical window so as to allow the UV light to strike the monitor electrodes. The UV light is blocked from propagating through an electrical field between the monitor electrodes.

In accordance with another aspect of the invention, the PID additionally includes electronic circuitry for the operation of the PID. A bias circuit biases the electrodes of the ion detector and the UV monitor to induce an electrical field between each pair of electrodes. A measurement circuit senses the currents for measuring the concentration of the ionized gases as well as the intensity of the UV light. The measurement circuit provides a signal indicative of the currents to a microprocessor. A pump and lamp driver circuit, connected to the lamp and the pump, respectively, also communicate with the microprocessor.

In accordance with still another aspect of the invention, a method for producing electrodes for the ion detector and the UV monitor includes forming an electrode layer on a substrate, selectively patterning the electrode layer to produce an interdigital electrode structure, and removing the substrate from the interdigital electrode structure. Alternatively, the substrate can be patterned to match the shape of the interdigital electrodes. Alternatively, the substrate may be transparent to UV light.

In accordance with still another aspect of the invention, a method for self-cleaning the PID and the optical windows of the ionization and UV monitor chambers includes introducing a gas containing oxygen into the ionization chamber, transmitting UV light into the ionization chamber to create ozone, and allowing the ozone to accumulate in the ionization chamber. Ozone is a strong oxidant which etches and removes the contamination from surfaces, including the optical windows, of the ionization chamber.

DESCRIPTION OF THE PREFERRED EMBODIMENTS

Figure 1:
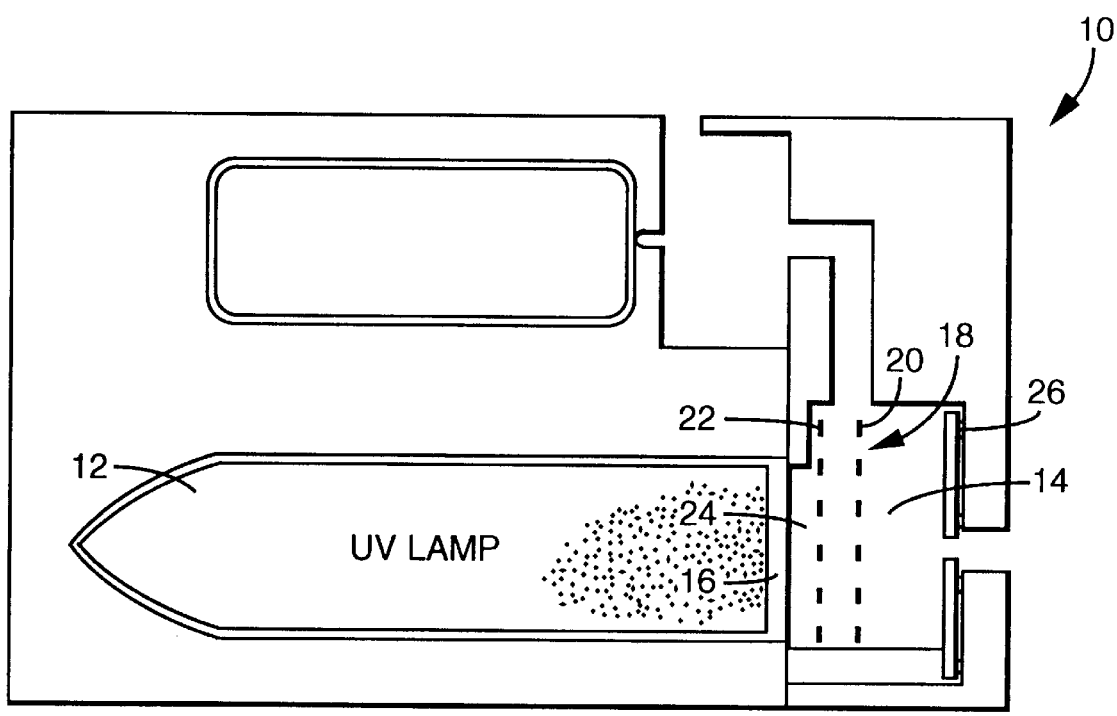
FIG. 1 is a block diagram of a conventional photo-ionization detector (PID)
Figure 2:
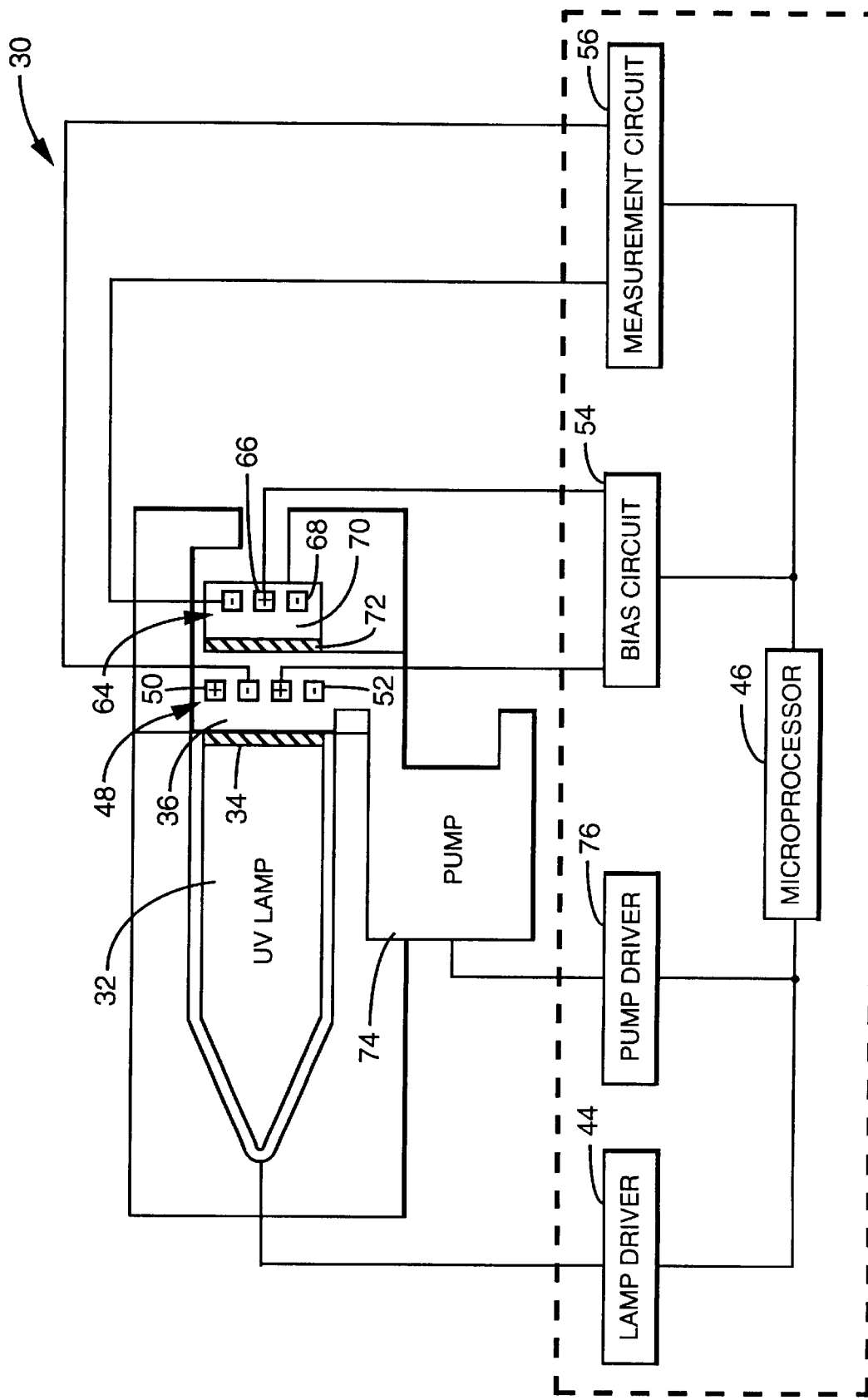
FIG. 2 is a block diagram of a PID of the present invention.
Figure 3:
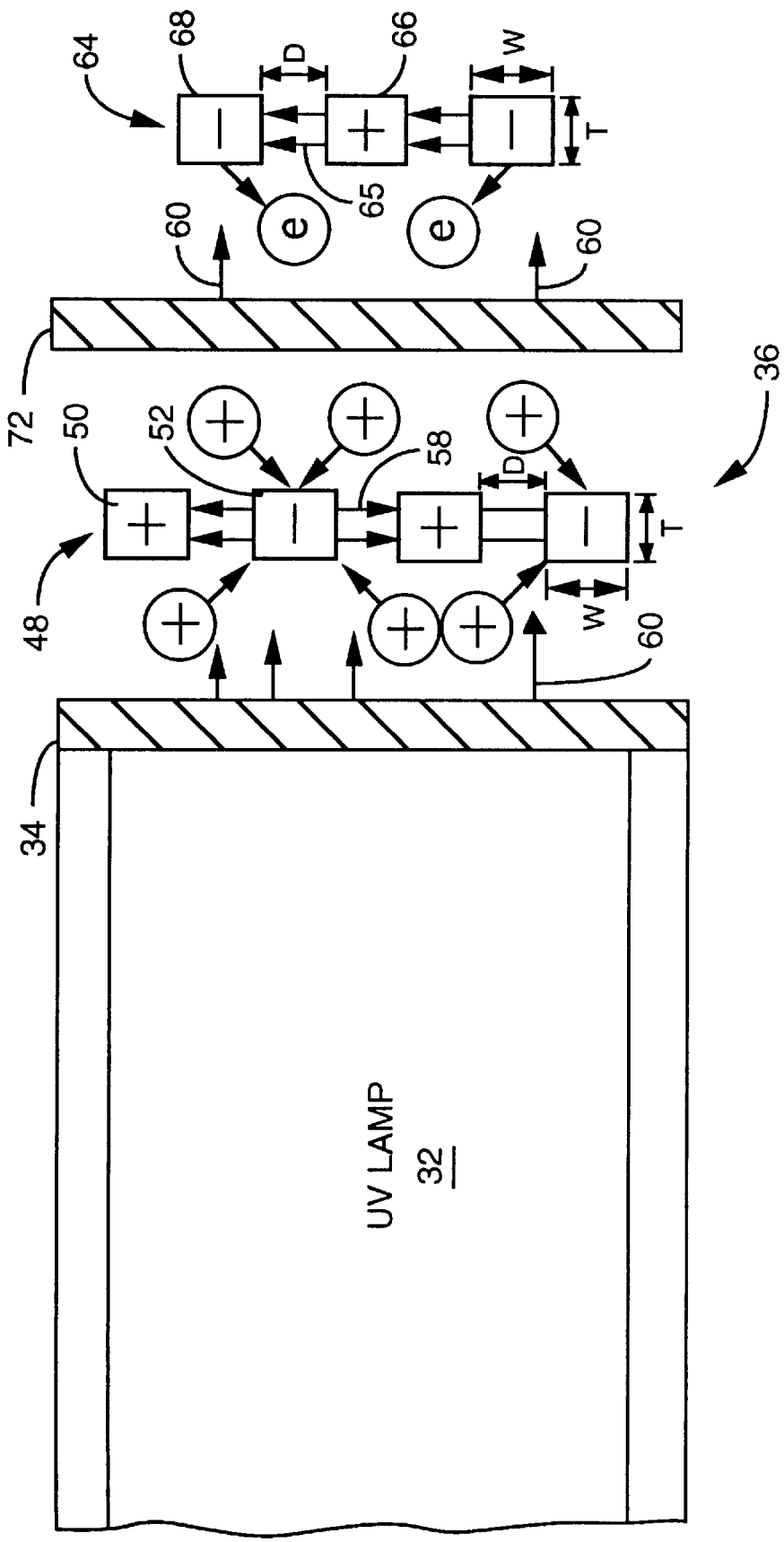
FIG. 3 is a schematic cross sectional view of an ionization chamber, having an ion detector, and an ultraviolet (UV) monitor chamber, having a UV monitor, for the PID of FIG. 2.
Figure 4:
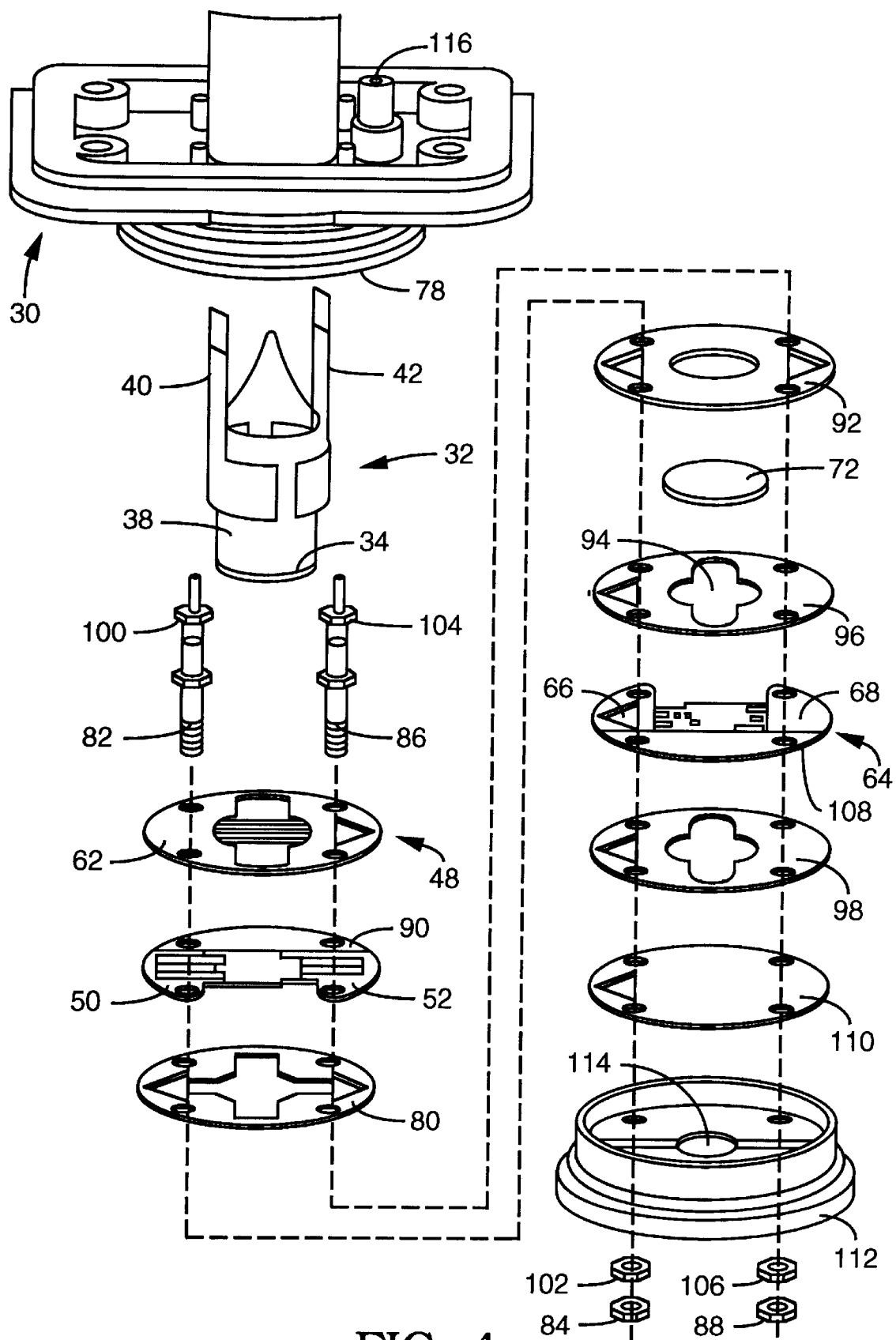
FIG. 4 is an expanded perspective view of a PID in accordance with the present invention.

In the drawings, similar parts are identified by like reference numerals. FIGS. 2 to 4 show a photo-ionization detector (PID) 30 in accordance with an embodiment of the invention. PID 30 is a "pocket" size, portable detector of volatile gases. To reduce the size and energy requirement and to increase the accuracy, PID 30 includes an improved ultraviolet (UV) lamp 32 that radiates UV photons or UV light 60 (light having a wavelength less than about 150 nm) through an optical window 34 into an ionization chamber 36. As illustrated in FIG. 4, UV lamp 32 includes a sealed envelope 38, preferably manufactured from glass. Envelope 38 contains a mixture of inert gases such as helium (e.g., 40%), argon (e.g., 30%) and krypton (e.g, 30%), at a reduced pressure (e.g., 25 Torr). Illustrative dimensions for envelope 38 include 0.25–0.5 inch diameter and 0.5–1.50 inch length. Optical window 34 is disposed at the end of envelope 38 and is made of a single crystal material. For example, optical window 34 may be manufactured from lithium fluoride (LiF), magnesium fluoride ($MgF_2$), barium fluoride ($BaF_2$), or calcium fluoride ($CaF_2$) which are capable of allowing the transmission of photons having energies of 11.7 electron volts (eV), 10.6 eV, 9.8 eV, and 9.2 eV, respectively. UV lamp 32 is disposed between two plates or driver electrodes 40 and 42 which are connected to a lamp driver circuit 44. Driver electrodes 40 and 42 may be manufactured from copper plates, measuring, for example, 0.20 inches by 0.20 inches. Lamp driver circuit 44 provides to driver electrodes 40 and 42 an AC signal of about 650–1250 V at a frequency of about 100 kHz. Consequently, a strong electrical field is created inside envelope 38 which ionizes the inert gases. The electrons and the ions inside envelope 38 recombine to generate UV photons in a process known as glow discharge. Depending on the material of choice for optical window 34, UV photons having a desired energy level pass through optical window 34. Lamp driver circuit 44 for generating the high voltage AC signal across plates 40 and 42 is described in U.S. Pat. No. 5,773,833 to Hsi, assigned to the assignee of the present invention, and incorporated herein by reference in its entirety. A microprocessor 46 can adjust the high voltage AC signal that is applied to plates 40 and 42, and thereby adjust the UV intensity of UV lamp 32. In accordance with another aspect of the present invention, microprocessor 46 may be used to minimize the energy consumed by UV lamp 32. In a typical gas discharge lamp, the AC voltage required to start the glow discharge is usually higher (10 to 20% more) than the voltage required to sustain the glow discharge. Microprocessor 46, via lamp driver circuit 44, can start UV lamp 32 using more power (higher AC voltage) and then decrease the power (lower AC voltage) to sustain the glow discharge.

Another energy saving feature of UV lamp 32 is that driver electrodes 40 and 42 are insulated from the ions and the electrons inside envelop 38 during the glow discharge process. Accordingly, no DC current flows between driver electrodes 40 and 42, and initiating and sustaining the glow discharge does not suffer from energy loss due to the DC current. Miniaturization of UV lamp 32 and envelope 38 also saves power because smaller gas volumes require less energy to initiate and sustain the glow discharge. Envelope 38 is easily miniaturized because no electrodes or other devices are required inside envelope 38, and the total power consumed by lamp driver circuit 44 and UV lamp 32 can be less than 100 mW.

Figure 5A:
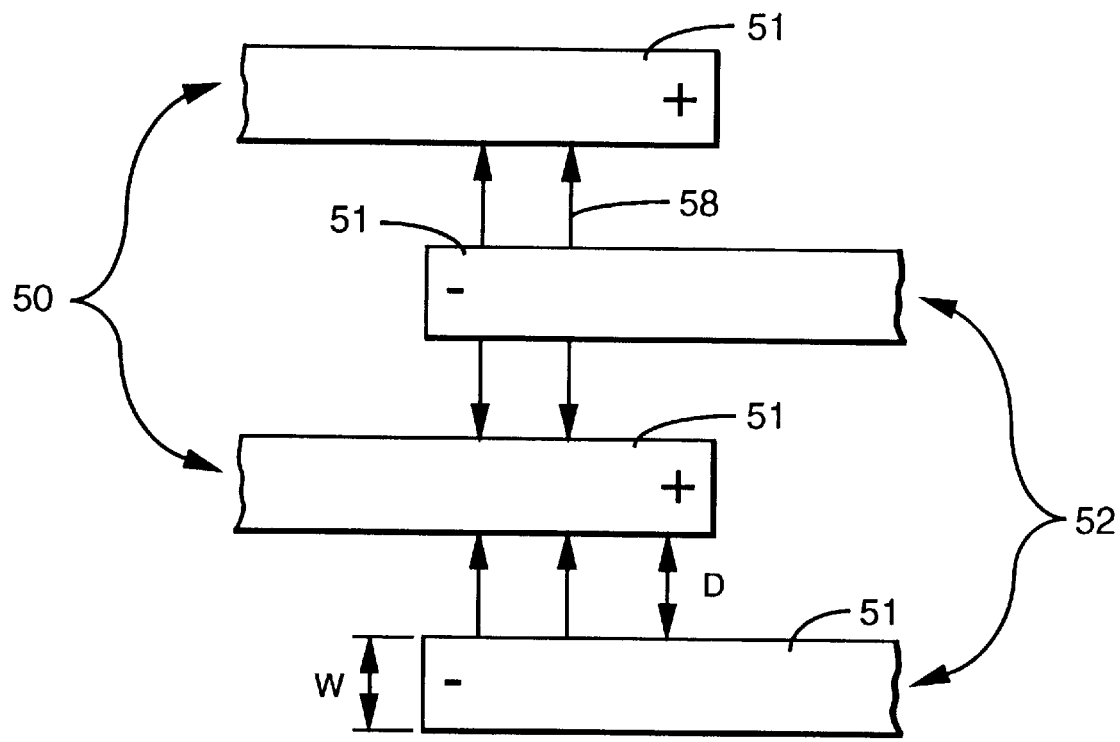
FIG. 5A is a partial end elevational view of one embodiment of the ion detector, having interdigital electrodes.
Figure 5B:
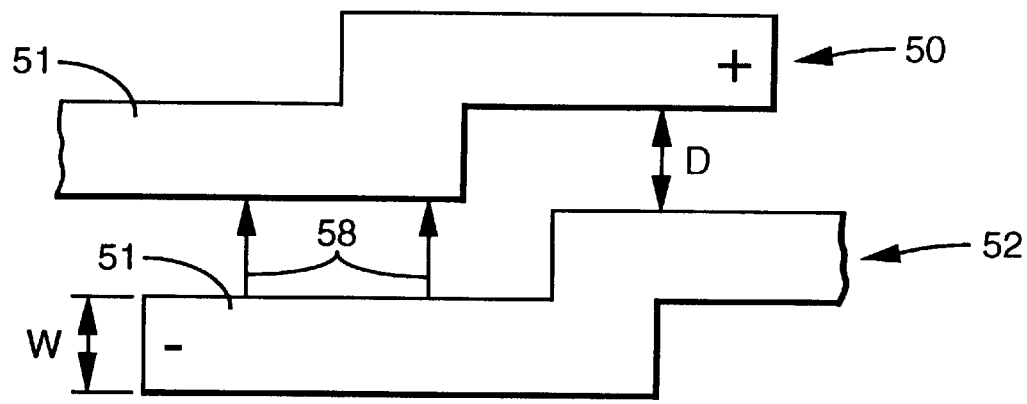
FIG. 5B is a partial end elevational view of another embodiment of the ion detector, having interdigital electrodes.

As discussed above, UV photons from UV lamp 32 ionize volatile gas molecules which are inside ionization chamber 36. An ion detector 48 disposed in ionization chamber 36 and positioned proximal to optical window 34 collects the resulting electrons and ions. Ion detector 48 comprises a pair of electrodes, a bias electrode 50 and a measurement electrode 52. As illustrated in FIGS. 3, 4, 5A and 5B, each bias and measurement electrode 50 and 52 has at least a pair of digits 51, positioned in an interdigital arrangement. Digits 51 of bias and measurement electrodes 50 and 52 can be linear or straight, as illustrated in FIG. 5A, or non-linear, as illustrated in FIG. 5B. Even though FIG. 5B illustrates digits 51 having a "step-like" shape, it is understood that digits 51 may have other patterns or shapes. It is further understood that bias and measurement electrodes 50 and 51 can each have from one to a plurality of digits 51. Digits 51 can be formed by machine manufacturing various metals and alloys, preferably stainless steel. Bias and measurement electrodes 50 and 52 can also be formed by depositing a conductive electrode layer on a substrate, masking selected portions of the electrode layer, and etching and removing the remaining portions from the substrate to produce the interdigital electrode pattern. Subsequent to the etching process, the substrate is removed from the produced interdigital electrode. Alternatively, a transparent substrate may be used that allows UV light to be transmitted therethrough, thus avoiding the removal of the substrate. Alternatively, portions of the substrate can be removed to form a pattern that matches the interdigital electrode in shape. Examples of material used for the electrode layer and substrate include platinum on a ceramic substrate, copper on a printed circuit board or gold on a silicon wafer. Illustrative dimensional specification of bias and measurement electrodes 50 and 52 includes about 0.01 to about 0.20 inches in thickness T, most preferably about 0.02 inches in thickness, and about 0.01 to about 0.08 inches in width W, most preferably about 0.02 inches in width. The distance or separation D between digits 51 of bias and measurement electrodes 50 and 52 is about 0.01 to about 0.20 inches, most preferably about 0.03 inches (see FIGS. 3 and 5A). It is understood that these measurement are illustrative in nature and that bias and measurement electrodes 50 and 52 can have other thickness, width, and separation.

A bias circuit 54 provides a positive bias voltage (e.g., DC voltage of about 4–120V) to bias electrode 50. As a result, bias electrode 50 repels positive ions formed by photoionization. Measurement electrode 52 is near ground voltage and separated from bias electrode 50 to create an electrical field 58 between bias electrode 50 and measurement electrode 52. Measurement electrode 52 attracts the positive ions which produce a measurement current. A measurement circuit 56, the preferred embodiment of which is disclosed in the above-incorporated 5,773,833 patent, is connected to measurement electrode 52 and measures the electrical current caused by the collection of the ions, i.e., the measurement current. Microprocessor 46 communicates with both bias circuit 54 and measurement circuit 56 and can adjust the bias voltage that bias circuit 54 applies to bias electrode 50. From measurement circuit 56, microprocessor 46 receives a signal indicative of the measurement current in order to determine the volatile gas concentration.

Electrical field 58 between electrodes 50 and 52, as illustrated in FIG. 3, is perpendicular to the direction of propagation of UV light 60. The perpendicular relationship of electrical field 58 and UV light 60 propagation allows ion detector 48 to be more sensitive to the ionizable gases for accurate measurements. In particular, ion detector 48 can accurately measure concentration ranges up to about 10,000 ppm of ionizable gases. Arranging bias electrode 50 and measurement electrode 52 in the manner as illustrated in FIGS. 2–5B eliminates "dead zones," or areas within ionization chamber 36 in which volatile gases and/or positive ions become trapped.

UV light 60 striking ion detector 48 can liberate electrons from bias and measurement electrodes 50 and 52. Electrons liberated from bias electrode 50 are, in general, attracted back to bias electrode 50 and do not contribute to a base line current (i.e., a current presented even in the absence of ionizable gases). However, electrons liberated from measurement electrode 52 can lead to a base line current. Base line currents provide another variable that must be accounted for when determining volatile gas concentrations. Consequently, a UV shield 62 (see FIG. 4) may be positioned between optical window 34 and measurement electrode 52 to prevent UV light 60 from striking measurement electrode 52. Alternatively, a layer of material (not shown) which is inert to the gases and ions generated in ionization chamber 36, has an electrically insulative property, and is opaque to high energy UV light may be employed as a UV shield. For example, a photo-resist polymer or ceramic layer of polytetrafluoroethene (Teflon) or alumina may be formed on the surface of measurement electrode 52 facing optical window 34 to serve as a UV shield. The UV shield as just described may also be employed for bias electrode 50. In summary, the UV shield prevents UV light 60 from reaching the exposed surface of ion detector 48, without significantly restricting collection of ions and electrons by measurement electrode 52 and bias electrode 50, respectively.

A UV monitor 64 is inside ionization chamber 36 with ion detector 48 being between UV monitor 64 and optical window 34. UV monitor 64 is similar to ion detector 48, in that UV monitor 64 also comprises a pair of interdigital patterned electrodes—a bias electrode 66 and a measurement electrode 68. The interdigital pattern of bias and measurement electrodes 66 and 68 can be of the same shape and formed by the same process and material as measurement and bias electrodes 50 and 52 of the ion detector 48. Illustrative dimensional specification includes about 0.01 to about 0.20 inches in thickness T, most preferably 0.02 inches in thickness and about 0.01 to about 0.08 inches in width W, preferably about 0.03 inches. The distance or separation D between digits of bias and measurement electrodes 66 and 68 is about 0.01 to about 0.20 inches, preferably about 0.02 inches. It is understood that these measurement are illustrative in nature and that bias and measurement electrodes 66 and 68 can have other thickness, width, and separation. Similar to ion detector 48, bias circuit 54 also provides a positive bias voltage (e.g, DC voltage greater than about 4V) to bias electrode 66. Measurement electrode 68 is near ground voltage and separated from bias electrode 66 to create an electrical field 65 between bias electrode 66 and measurement electrode 68. Electrical field 65 is perpendicular in direction to the propagation of UV light 60. When UV light 60 strikes UV monitor 64, measurement electrode 68 emits electrons that bias electrode 66 collects, thus creating a monitor current. Measurement circuit 56, being connected to measurement electrode 68, measures the monitor current and communicates to microprocessor 46 a signal indicative of the current and the intensity of UV light 60. In one embodiment, microprocessor 46 performs a procedure which incorporates the UV intensity variations when calculating the volatile gas concentration. It should be noted that UV intensity can vary for a variety of reasons, including depreciation of the electrical performance of UV lamp 32, contamination of optical window 34 by polymer-like substances, and presence of interfering substances (i.e., substances which can absorb or enhance UV photons, e.g., methane, water, carbon monoxide, nitrogen, etc.). In another embodiment, in lieu of or in addition to applying the UV intensity variations in calculating gas concentrations, microprocessor 46 adjusts the output voltage of lamp driver circuit 44 to increase or decrease the power of UV lamp 32 so as to maintain a constant UV intensity.

Because measurement electrode 68 of UV monitor 64 has a near ground potential, positive ions of the ionized gases are attracted to measurement electrode 68. The positive ions increase the monitor current. When this occurs, the monitor current is no longer an accurate reflection of the intensity of UV light 60. As a result, microprocessor 46 must be programmed to carry-out correction protocols in estimating the UV intensity, two of which are disclosed in the above-incorporated 5,773,883 patent. In order to achieve a more accurate measurement of the UV intensity, UV monitor 64 is positioned inside a monitor chamber 70, wherein UV monitor 64 is sealed from any significant exposure or contact to the gases flowing through ionization chamber 36. UV monitor chamber 70 comprises an optical widow 72, positioned adjacent to UV monitor 64 for allowing UV light 60 to be transmitted therethrough and received by UV monitor 64. Should any gas penetrate into monitor chamber 70, the alignment of electrodes 66 and 68 of UV monitor 64 with respect to electrodes 50 and 52 of ion detector 48 prevents such gases from ionizing inside monitor chamber 70. The ionization of volatile gases occurs in an electrical field between a pair of differentially biased electrodes when struck by UV light. Interdigital electrodes 50 and 52 of ion detector 48 prevent UV light 60 from propagating onto electrical field 65 of UV monitor 64. In other words, the alignment of bias and measurement electrodes 66 and 68 with respect to bias and measurement electrodes 50 and 52 causes UV light 60 to propagate only on bias and measurement electrodes 66 and 68 and not on electrical field 65. Accordingly, gases leaking into the monitor chamber 70 are not ionized.

PID 30 also includes a built-in pump 74 (FIG. 2) which provides a flow of gases (e.g., 200–600 ml/min) into and out of ionization chamber 36. Accordingly, ionization chamber 36 is an open volume chamber, receiving a laminar flow of gases. When pump 74 is turned off, the ionization chamber 36 is closed volume, such that gases are prevented from flowing into or out of ionization chamber 36. The laminar flow of gases through ionization chamber 36 (out of the paper in FIGS. 2 and 3) is parallel to a plane defined by the surface of the optical window 34. Furthermore, the flow of gases is perpendicular to electrical field 52 of bias and measurement electrodes 50 and 52. Thus, gases flow easily between bias and measurement electrodes 50 and 52 and more ions are collected by measurement electrode 52. The flow of gases is also perpendicular to the direction of propagation of UV light 60. Accordingly, the perpendicular relationship between UV light 60 and the gas flow facilitates ionization of a greater percentage of gas molecules between electrodes 50 and 52 and also allows for a greater collection of the ion molecules by measurement electrode 52. Pump 74 is connected to a pump driver circuit 76 which in turn is connected to microprocessor 46 for controlling pump 74.

In addition to controlling pump driver circuit 76, lamp driver circuit 44, bias circuit 54, and receiving signals from measurement circuit 56, microprocessor 46 may also execute firmware. The firmware provides a user interface for controlling PID 30, displaying volatile gas concentration, and generating warning signals if the volatile gas concentration reaches designated threshold levels. Controls, an alarm, and a liquid crystal display (not shown) provide a hardware portion of the user interface. A non-volatile memory such as a ROM, EEROM, or Flash Memory (not shown) contains the firmware and parameters for calibration of PID 30. A volatile memory may also be required unless microprocessor 46 contains sufficient on-chip memory for execution of the firmware.

FIG. 4 shows an expanded perspective drawing of the components in an exemplary embodiment of PID 30. By way of illustration and not limitation, PID 30 of the present invention is a "pocket" sized PID which measures 7.75 inches in length by 2.75 inches in width by 1.50 inches in height. PID 30 weighs 18 ounces and is powered by a nickel metal hydride battery pack (not shown) which can provide about 10–12 hours of continues operation. UV lamp 32, including optical window 34, glass envelope 38, and driver electrodes 40 and 42 are contained in a PID housing 78. Pump 74 (not shown), measuring 1.40 inches in length, 0.70 inches in width, and 1.00 inches in height, and weighing at about 2 ounces, may be incorporated into PID housing 78. In this embodiment, ionization chamber 36 provides a free volume of about 5 micro-liters. Bias and measurement electrodes 50 and 52 of ion detector 48 are positioned parallel to each other and disposed between UV shield 62 and a first insulation spacer 80. Bias electrode 50 connects to bias circuit 54 via a connecting pin 82 and a nut 84. Measurement electrode 52 is maintained at near ground voltage and connects to measurement circuit 56 via a pin 86 and a nut 88. Bias and measurement electrodes 50 and 52 attach or abut to an alignment sheet 90. Alignment sheet 90 keeps bias and measurement electrodes 50 and 52 parallel to each other. A gasket 92 separates ionization chamber 36 from UV monitor chamber 70. UV monitor chamber 70 comprises optical window 72 positioned over an opening 94 of a second insulation spacer 96. Bias and measurement electrodes 66 and 68 of UV monitor 64 are parallel to each other and disposed between second insulation spacer 96 and a third insulation spacer 98. Bias electrode 66 connects to bias circuit 54 via a connecting pin 100 and a nut 102. Measurement electrode 68 connects to measurement circuit 56 via a pin 104 and a nut 106 and is maintained at near ground voltage. Bias and measurement electrodes 66 and 68 also attach or abut to an alignment sheet 108 that keeps bias and measurement electrodes 66 and 68 parallel to each other. A solid spacer 110 encloses UV monitor chamber 70. UV shield 62 may be manufactured from a polytetrafluoroethene (Teflon) sheet having a thickness of about 0.02 inches and a diameter of about 1.50 inches. Alignment sheets 90 and 108, spacers 80, 96, and 98, gasket 92, and solid spacer 110 may have a thickness of about 0.02 inches and a diameter of about 1.50 inches and may be manufactured from an insulating material that is inert to volatile gases and ions, and is opaque to the high energy UV light. For example, the material may include acrylonitril butadiene styrene, polycarbonate, polyethelyne, polypropylene, polyurethane, and polyvinyl chloride. Preferably, the material is Teflon. An end cap unit 112 enclosed ionization chamber 36 and UV monitor chamber 70 within PID housing 78. End cap unit 112 has a gas inlet 114 and housing 78 has an gas outlet 116 for allowing pump 74 to circulate the gases through ionization chamber 36.

PID 30 should be initialized or calibrated before operation. PID 30 may be initialized or calibrated by the "zero gas" or known sample calibration methods, both which are well understood in the art. For example, a user can place PID 30 in a "zero gas" calibration mode. During "zero gas" calibration, a clean dry air sample which contains no ionizable volatile gases and no interfering substances (e.g., methane, water, etc.) is passed through ionization chamber 36. Measurement circuit 56 receives a measurement current and communicates a signal indicative of the measurement current to microprocessor 46. The signal should have a value very close to zero because the sample of gas does not contain any ionizable gases and UV shield 62 protects ion detector 48 from forming a baseline current.

"Zero gas" calibration also provides a reference level for the monitor current. UV monitor 64 detects photons from UV lamp 32 which pass through UV shield 62 and ion detector 48 and reach measurement electrode 68 of UV monitor 64 without ionizing any volatile gas molecules or being absorbed by interfering substances. Such UV photons striking measurement electrode 68 free electrons to create a monitor current. Microprocessor 46 stores the signal indicative of the monitor current for the "zero gas" sample to establish a reference value to which subsequent monitor currents are compared.

The user can also calibrate PID 30 with a sample having a known concentration of volatile gas molecules. When a known sample of gas molecules is introduced into ionization chamber 36, the resulting measurement and monitor currents may be observed. Accordingly, microprocessor 46 can determine a proportionality constant between the measured values and the known values of the measurement and monitor currents for the given concentration of gases. The proportionality constant is stored in microprocessor 46 and is subsequently used to determine volatile gas concentrations.

During the normal operation of PID 30, the effectiveness of PID 30 diminishes due to the build-up of contamination in ionization chamber 36, including on the bias and measurement electrodes 50 and 52. The UV intensity, moreover, gradually decreases due to the build-up of such contamination on the surfaces of optical windows 34 and 72. Typically, the contamination includes a coating of metal atoms, oil film, dust particles, or other polymer-like coating substances. As a result, a user must often clean ionization chamber 36, including optical windows 34 and 72. The present invention additionally provides a method for self-cleaning ionization chamber 36, including bias and measurement electrodes 50 and 52 and optical windows 34 and 72. After using PID 30, microprocessor 46 can be programmed to turn pump 74 off while maintaining transmission of UV lamp 32. Because pump 74 is turned off, gases are prevented from entering into and exiting out of the closed volume of ionization chamber 36. UV light 60 converts oxygen, enclosed in ionization chamber 36, to ozone. Ozone, a strong oxidant, accumulates in ionization chamber 36 and oxidizes, i.e., etches and removes, contamination from ionization chamber 36, including surfaces of bias and measurement electrodes 50 and 52 and optical windows 34 and 72. After the contamination has been etched and removed, pump 74 is turned on to flush and discharge the contamination out of ionization chamber 36. The self-cleaning process removes contamination practically without any user involvement.

While particular embodiments of the present invention have been show and described, changes and modifications may be made without departing from this invention in its broader aspects and, therefore, the appended claims are to encompass within their scope all such changes and modifications as fall with the true spirit and scope of this invention.

What is claimed is:

1. A photo-ionization detector (PID) comprising:
   (a) a detector housing having an ionization chamber disposed therein, said ionization chamber configured to allow gases to flow into and out of said ionization chamber;
   (b) an ultraviolet (UV) lamp positioned to transmit a UV light into the ionization chamber;
   (c) an ion detector disposed in said ionization chamber, said ion detector comprising a first electrode structure electrically biased to attract negatively charged particles, and a second electrode structure electrically biased to attract positively charged particles, wherein an electrical field between said first electrode structure and said second electrode structure is perpendicular to a direction of propagation of said UV light and wherein said electrical field is perpendicular to a direction of flow of gases.

2. The PID of claim 1, wherein said ionization chamber is adjustable between an open and closed volume position, said open volume position allows gases to flow into and out of said ionization chamber, said closed volume position prevents gases from flowing into and out of said ionization chamber.

3. The PID of claim 2, wherein said UV light propagating in said ionization chamber produces ozone from oxygen contained in said ionization chamber when said ionization chamber is in said closed volume position.

4. The PID of claim 2, wherein said flow of gases is laminar through said ionization chamber when said ionization chamber is in said open volume position.

5. The PID of claim 1, wherein said UV lamp comprises:
   (a) a sealed envelope enclosing a quantity of gas, said sealed envelope including an optical window which is transparent to a desired frequency of said UV light and is positioned adjacent to said ionization chamber; and
   (b) a pair of driver electrodes which are electrically insulated from each other and placed outside said sealed envelope to provide an electric field which induces a glow discharge process within said sealed envelope.

6. The PID of claim 1, additionally comprising a measurement circuit communicating with said second electrode structure of said ion detector.

7. The PID of claim 1, additionally comprising a UV monitor.

8. The PID of claim 7, additionally comprising a UV monitor chamber enclosing said UV monitor, wherein said gases do not significantly penetrate into said UV monitor chamber, said UV monitor chamber including an optical window for allowing said UV light to be transmitted therethrough and received by said UV monitor.

9. The PID of claim 7, wherein said UV monitor comprises a first electrode structure electrically biased to attract negatively charged particles and a second electrode structure electrically biased to attract positively charged particles.

10. The PID of claim 9, wherein said UV light does not significantly propagate on an electrical field between said first and second electrode structures of said UV monitor.

11. The PID of claim 9, additionally comprising a measurement circuit for measuring a monitor current through said second electrode structure of said UV monitor and a measurement current through said second electrode structure of said ion detector.

12. The PID of claim 1, additionally comprising a shield that prevents said UV light from striking said first electrode structure of said ion detector.

13. The PID of claim 12, wherein said shield comprises a layer of alumina formed on at least a portion of said first electrode structure of said ion detector.

14. The PID of claim 12, wherein said shield comprises a layer of polytetrafluoroethene formed on at least a portion of said first electrode structure of said ion detector.

15. The PID of claim 1, additionally comprising a shield that prevents said UV light from striking said second electrode structure of said ion detector.

16. The PID of claim 15, wherein said shield comprises a layer of alumina formed on at least a portion of said second electrode structure of said ion detector.

17. The PID of claim 15, wherein said shield comprises a layer of polytetrafluoroethene formed on at least a portion of said second electrode structure of said ion detector.

18. The PID of claim 1, additionally comprising a pump integrated into said detector housing to cause gases to flow into and out of said ionization chamber.

19. The PID of claim 1, additionally comprising a microprocessor that implements a self-cleaning process by keeping said pump off while said UV lamp remains on.

20. The PID of claim 1, wherein said direction of flow of gases is perpendicular to said direction of propagation of said UV light.

21. The PID of claim 1, wherein said first and second electrode structures of said ion detector comprise digits, and a substrate supporting said digits, said substrate processed in a pattern that matches said digits in shape.

22. The PID of claim 1, wherein said first and second electrode structures of said ion detector comprise digits, and a substrate supporting said digits, said substrate being transparent to said UV light.

23. A photo-ionization detector (PID) comprising:
   (a) an ionization chamber configured to receive gases;
   (b) an ultraviolet (UV) lamp positioned to transmit a UV light into said ionization chamber;

(c) an ion detector disposed in said ionization chamber; and (d) a UV monitor positioned to detect an intensity of said UV light, said UV monitor comprising a first electrode structure electrically biased to attract negatively charged particles and a second electrode structure electrically biased to attract positively charged particles.

24. The PID of claim 23, wherein said ion detector comprises a first electrode structure electrically biased to attract negatively charged particles and a second electrode structure electrically biased to attract positively charged particles, wherein a direction of an electrical field between said first and second electrode structures is perpendicular to a direction of propagation of said UV light.

25. The PID of claim 24, additionally comprising:

(a) a measurement circuit communicating with said second electrode structure of said ion detector to measure a measurement current; and (b) a microprocessor coupled to said measurement circuit, wherein said microprocessor uses said measurement current to determine a concentration of ionizable gas molecules.

26. The PID of claim 24, additionally comprising:

(a) a measurement circuit communicating with said second electrode structure of said ion detector to measure a measurement current and said second electrode structure of said UV monitor to measure a monitor current; and (b) a microprocessor coupled to said measurement circuit, wherein said microprocessor uses said measurement and monitor currents to determine a concentration of ionizable gas molecules.

27. The PID of claim 24, wherein said first and second electrode structures of said ion detector prevent said UV light from striking an electrical field between said first and second electrode structures of said UV monitor.

28. The PID of claim 24, additionally comprising a pump for causing a flow of gases into and out of said ionization chamber, wherein a direction of said flow of gases through said ionization chamber is perpendicular to the direction of said electric field between said first and second electrode structures of said ion detector and perpendicular to the direction of the propagation of said UV light.

29. The PID of claim 23, additionally comprising:

(a) a measurement circuit communicating with said second electrode structure of said UV monitor to measure a monitor current; and (b) a microprocessor coupled to said measurement circuit, wherein said microprocessor uses said monitor current to determine the UV intensity of said UV light in said ionization chamber.

30. The PID of claim 23, additionally comprising a UV monitor chamber enclosing said UV monitor, wherein said gases do not substantially leak in said UV monitor chamber.

31. The PID of claim 23, wherein an electrical field between said first and second electrode structures of said UV monitor is perpendicular to a direction of propagation of said UV light.

32. A photo-ionization detector (PID) comprising:

(a) a detector housing;

(b) an ionization chamber disposed in said housing for receiving gases;

(c) an ultraviolet (UV) lamp positioned to transmit a UV light into said ionization chamber;

(d) an ion detector disposed in said ionization chamber to detect ionized gases;

(e) a UV monitor positioned to be struck by said UV light; and (f) a monitor chamber containing said UV monitor, wherein said monitor chamber is sealed away from said ionization chamber so that said gases do not significantly contact said UV monitor.

33. A photo-ionization detector (PID) comprising:

(a) a detector housing;

(b) an ionization chamber disposed in said housing for receiving gases;

(c) an ultraviolet (UV) lamp positioned to transmit a UV light into said ionization chamber;

(d) an ion detector disposed in said ionization chamber to detect ionized gases; and (e) a UV monitor positioned in said ionization chamber to be struck by said UV light, wherein:

said gases do not significantly contact said UV monitor; and said UV monitor comprises a first electrode structure and a second electrode structure positioned at a selected distance from said first electrode structure to create an electrical field, wherein said UV light does not significantly contact said electrical field between said first and second electrode structures of said UV monitor.

34. A method for removing contamination from a photo-ionization detector (PID), said PID having an ionization chamber and a ultraviolet (UV) lamp used in detection of ionizable gas, comprising:

(a) introducing a gas containing oxygen into said ionization chamber of said PID;

(b) operating said UV lamp to transmit UV light into said ionization chamber, whereby said UV light converts oxygen to ozone in said ionization chamber; and (c) allowing said ozone to accumulate in said ionization chamber, whereby the ozone removes contamination.

35. The method of claim 34, additionally comprising, discharging said contamination from said ionization chamber.

36. The method of claim 34, additionally comprising providing at least one optical window in said ionization chamber and removing contamination from said at least one optical window.

37. A method for removing a coating deposited on surfaces of an ionization chamber and an optical window for a photo-ionization detector (PID), said PID comprising a pump to create a flow of gases into and out of said ionization chamber and an ultraviolet (UV) lamp positioned to transmit a UV light into said ionization chamber, the method comprising:

(a) turning off said pump; and (b) transmitting UV light in said ionization chamber to generate ozone, wherein said ozone removes said coating form said surfaces.

38. The method of claim 37, additionally comprising trapping oxygen in said ionization chamber and preventing gases from flowing into and out of said ionization chamber.

39. The method of claim 37, additionally comprising, subsequent to removing said coating, turning on said pump to flush said coating from said ionization chamber.

* * * * *